United States Patent
Bennett et al.

(10) Patent No.: US 6,460,275 B1
(45) Date of Patent: Oct. 8, 2002

(54) ORTHOTIC INSERT

(76) Inventors: W. Scott Bennett, 838 E. End Rd., Strawberry Plains, TN (US) 37871; Mary Lee Evers, 303 Fountain Ave., Paducah, KY (US) 42001; John H. Krusenklaus, 7260 Brickey La., Knoxville, TN (US) 37918

(*) Notice: Subject to any disclaimer, the term of this patent is extended or adjusted under 35 U.S.C. 154(b) by 0 days.

(21) Appl. No.: 09/795,900

(22) Filed: Feb. 28, 2001

(51) Int. Cl.[7] ............................................... A61F 5/14
(52) U.S. Cl. ........................ 36/144; 36/37; 36/30 R; 36/80
(58) Field of Search ..................... 36/144, 37, 30 R, 36/80, 28, 35 R, 44

(56) References Cited

U.S. PATENT DOCUMENTS

| | | | |
|---|---|---|---|
| 1,741,419 A | * 12/1929 | Jones | 36/145 |
| 2,031,510 A | * 2/1936 | Stewart et al. | 36/176 |
| 2,260,377 A | * 10/1941 | Herbst | 36/80 |
| 3,373,513 A | * 3/1968 | Jewell | 36/37 |
| 3,859,740 A | * 1/1975 | Kemp | 36/71 |
| 4,137,654 A | * 2/1979 | Hlavac | 36/117.5 |
| 4,235,028 A | * 11/1980 | Riggs | 36/69 |
| 4,346,525 A | 8/1982 | Larsen et al. | |
| 4,360,027 A | 11/1982 | Friedlander et al. | |
| 4,530,173 A | 7/1985 | Jesinsky, Jr. | |
| 4,747,410 A | 5/1988 | Cohen | |
| 4,882,856 A | 11/1989 | Glancy | |
| 4,928,404 A | * 5/1990 | Scheuermann | 36/35 R |
| 5,438,768 A | 8/1995 | Bauerfeind | |
| 5,713,143 A | 2/1998 | Kendall | |
| 5,766,251 A | 6/1998 | Koshino | |
| 6,038,793 A | 3/2000 | Kendall | |
| D448,850 S | * 10/2001 | Fabricant | D24/189 |

* cited by examiner

Primary Examiner—Ted Kavanaugh
(74) Attorney, Agent, or Firm—Luedeka, Neely & Graham P.C.

(57) ABSTRACT

An orthotic device for inserting within a heel portion of a shoe of a user for inhibiting excessive pronation or excessive supination of a user's foot, and for comforting associated pain by cushioning a heel of the foot, which includes a sloped wedge member with a cutout for receiving a portion of the heel of the user; and a cup member positionable adjacent the wedge member, the cup member including a cushion material therein located so as to substantially underlie the cutout of the wedge member when the cup member is positioned adjacent the wedge member.

12 Claims, 5 Drawing Sheets

ORTHOTIC INSERT

FIELD OF THE INVENTION

The present invention relates to orthotic devices. More particularly, the invention relates to devices for inhibiting excessive foot motion and for relieving pain associated with the excessive foot motion.

BACKGROUND AND SUMMARY OF THE INVENTION

Pronation of a human foot involves an inward rolling motion of the foot as it contacts the ground during a gait cycle. Supination involves an outward rolling motion of the foot as it contacts the ground during a gait cycle. Pronation and supination of the foot normally occur during the gait cycle and are generally observed as rotation of the heel bone or calcaneus, e.g., during pronation the heel rotates outwardly and during supination the heel rotates inwardly.

Excessive pronation or supination of the foot is undesirable and may cause discomfort and injury. Common maladies resulting from excessive foot motion include heel pain, knee pain, shin splints, and stress fractures. For example, heel pain is commonly associated with a condition known as plantar fascitiis, which is an inflammation of the plantar fascia ligament running along the bottom of the foot between the calcaneus and the metatarsal phalangeal joint. This inflammation is often associated with excessive foot pronation.

Attempts have been made to provide orthotic devices for counteracting excessive pronation and/or supination and for treating symptoms associated with these conditions. However, there remains a need in the art for devices for inhibiting excessive foot motion and for relieving pains associated with the excessive foot motion.

Accordingly it is an object of the present invention to provide an improved orthotic device.

Still another object of the present invention is to provide a device of the character described that is suitable for counteracting excessive pronation or supination and which tends to relieve pain associated with the excessive pronation or supination.

Yet another object of the invention is to provide a device of the character described that relieves pain by dispersing heel strike forces during the gait cycle.

A still further object of the invention is to provide a device of the character described that is economical to produce and uncomplicated in configuration.

With regard to the foregoing and other objects, the present invention is directed to an orthotic device for inserting within a heel portion of a shoe of a user for inhibiting excessive pronation or excessive supination of a user's foot, and for comforting associated pain by cushioning the heel.

In a preferred embodiment, the orthotic device includes a wedge member and a cup member positionable adjacent the wedge member.

The wedge member has an upper surface, an opposite lower surface, a front end, a heel end, a pair of opposite sides, and a cutout extending between the upper surface and the lower surface for receiving a portion of the heel of the user. The upper surface of the wedge member is sloped to define a substantially constant angle of from about negative 15 degrees to about 15 degrees to counteract the tendency of the foot to either excessively supinate or to excessively pronate.

The cup member includes an upper surface, an opposite lower surface, a front end, a heel end, a pair of opposite sides, and a shallow blind bore adjacent the lower surface of the cup member and extending toward the upper surface of the cup member and located so as to substantially underlie the cutout of the wedge member when the cup member is positioned adjacent the wedge member. The bore is substantially filled with a cushion material.

BRIEF DESCRIPTION OF THE DRAWINGS

Further advantages of the invention will become apparent by reference to the detailed description of preferred embodiments when considered in conjunction with the figures, which are not to scale, wherein like reference numbers, indicate like elements through the several views, and wherein.

DETAILED DESCRIPTION

Figure 1:
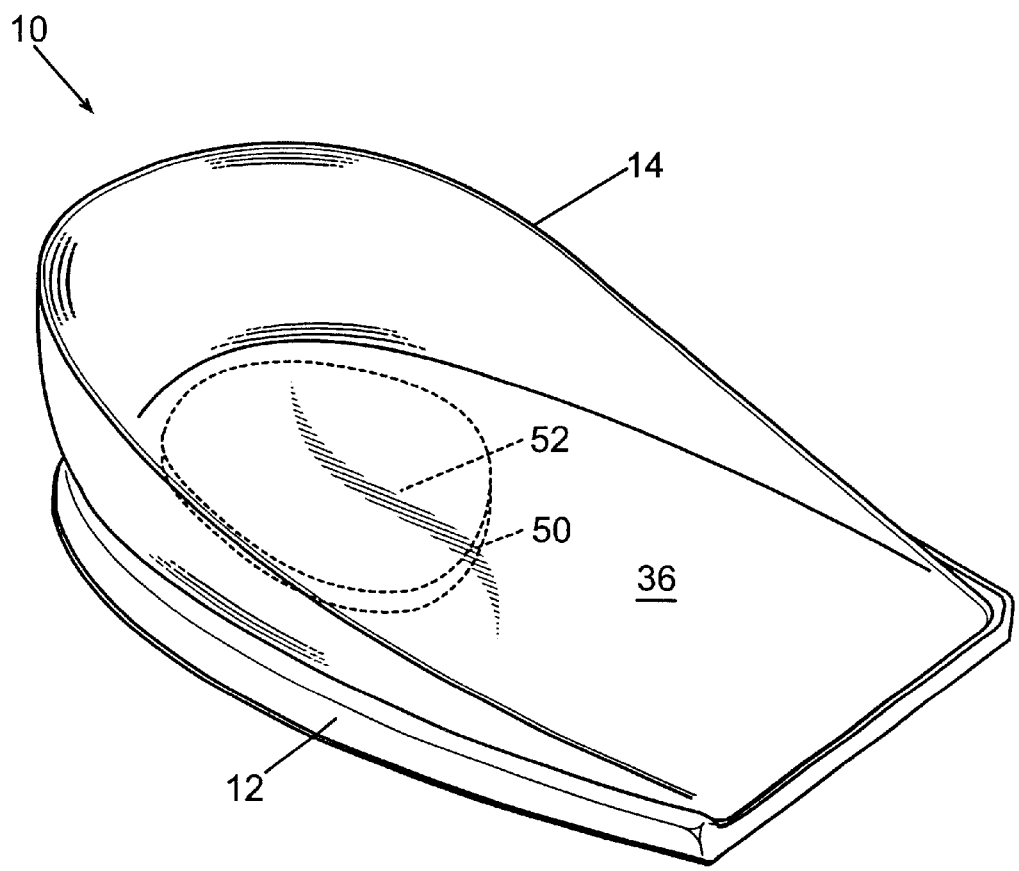
FIG. 1 is a perspective view of an orthotic device in accordance with a preferred embodiment the invention.
Figure 2:
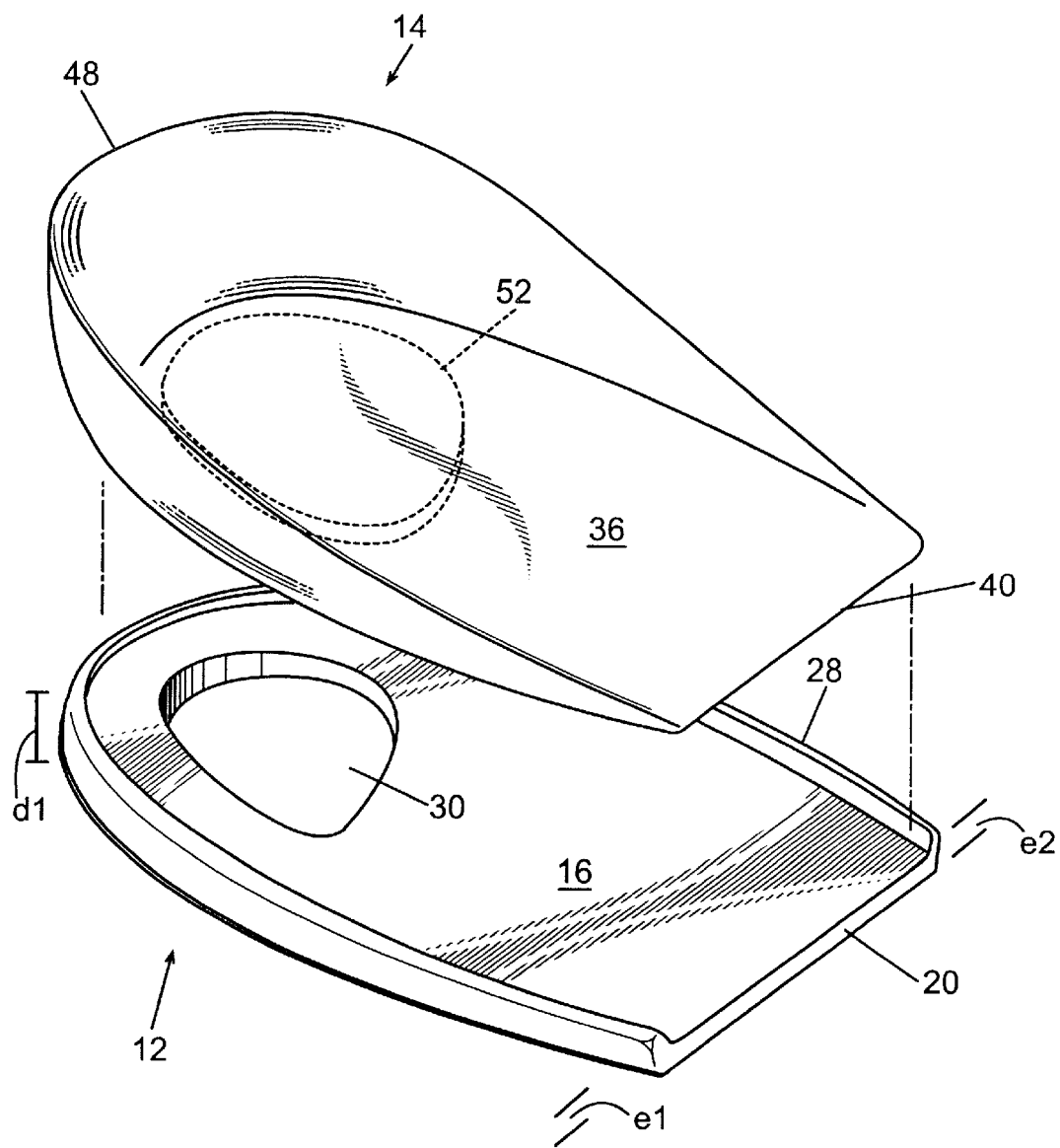
FIG. 2 is an exploded view of the device of FIG. 1.

With initial reference to FIGS. 1–2, the invention relates to an orthotic device 10 that is particularly suitable for treating mechanical foot conditions of the type characterized by excessive foot motion, such as excessive pronation or excessive supination, and for comforting associated pain, as by cushioning the heel of the foot of a user. The orthotic device 10 includes a wedge member 12 and a cup member 14 removably positionable adjacent the wedge member 12.

Figure 3:
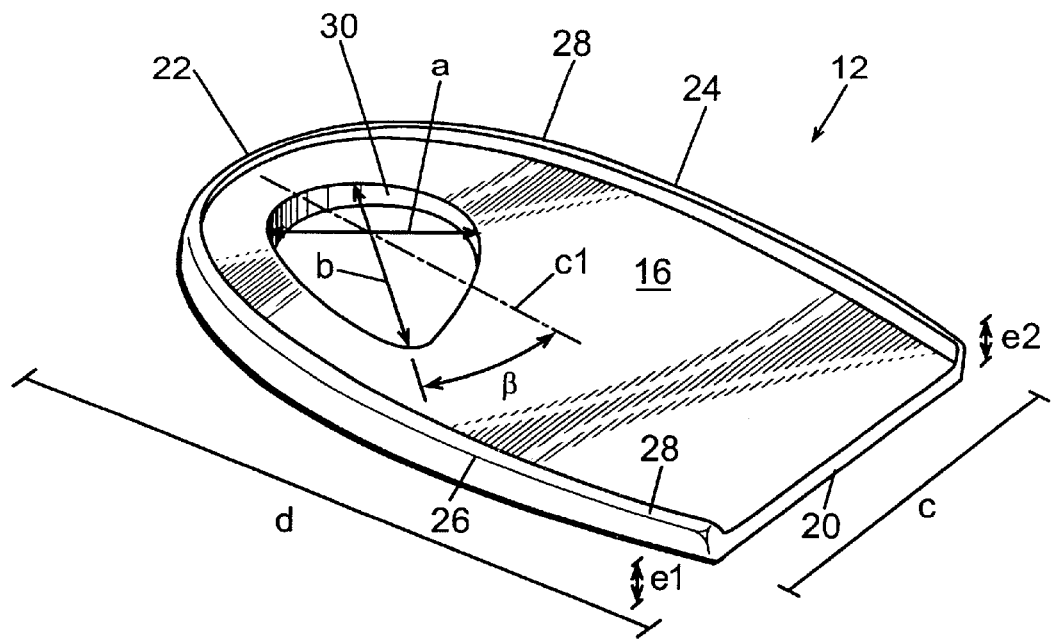
FIG. 3 is a top perspective view of a wedge component of the device of FIG. 1.
Figure 4:
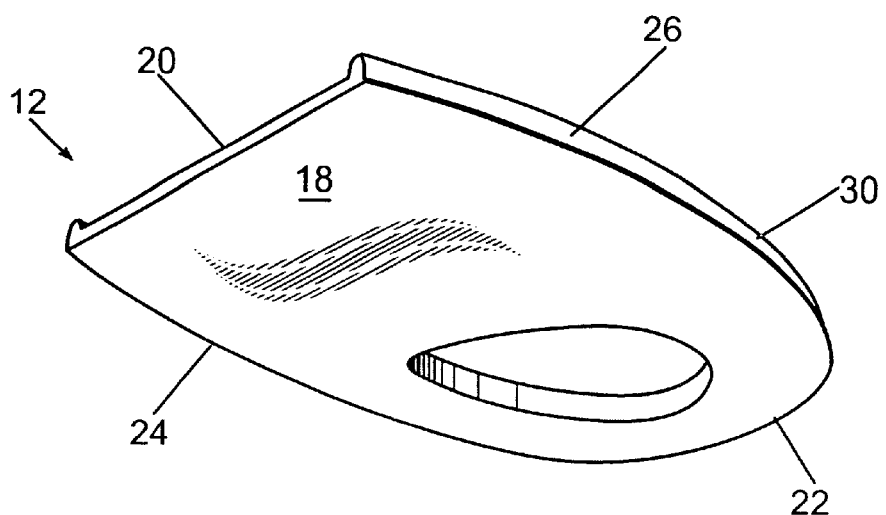
FIG. 4 is a bottom perspective view of the wedge component of FIG. 3.

With additional reference to FIGS. 3 and 4, the wedge member 12 is preferably of one-piece construction and made of a relatively stiff, yet flexible polymeric material. A preferred polymeric material is ethylene vinyl acetate (EVA).

The wedge member 12 is configured to fit within the heel area of a shoe and includes a substantially planar upper surface 16, an opposite substantially planar lower surface 18, a generally straight front end 20, a generally curved heel end 22 and a pair of slightly curved sides 24 and 26. The upper surface 16 preferably has minute ridges along its length or other rugosity to increase the coefficient of friction of the upper surface 16 to reduce relative motion, e.g., sliding, between the upper surface 16 and the cup member 14. In addition, a raised rib 28 preferably extends around the perimeter of the wedge member adjacent the end 22 and the sides 24 and 26 for contacting the side edges of the cup member 14 to inhibit relative motion. The rib 28 preferably has a height above the surface 16 of from about ⅛ to about ¼ inches, most preferably about 3/16 inch.

Figure 7:
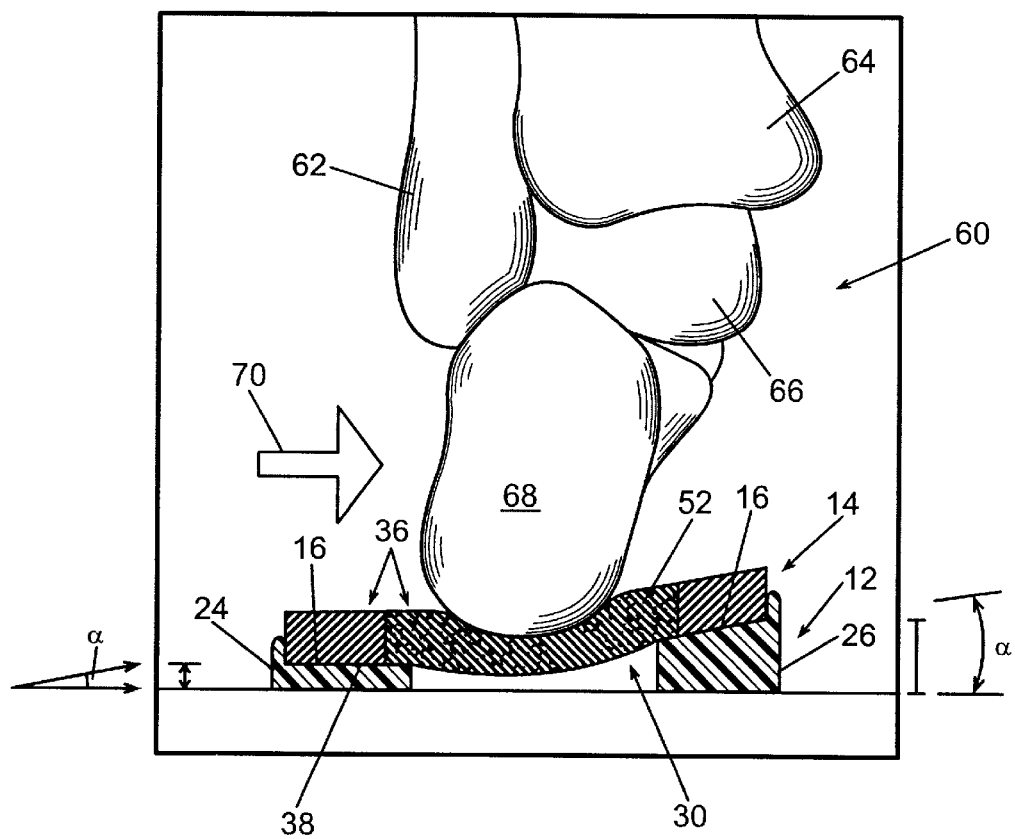
FIG. 7 is a posterior or view showing a rear cross-section of the device of FIG. 1 in use to inhibit excessive pronation of a human foot and to disperse heel strike forces.

As shown in FIG. 7, the upper surface 16 of the wedge member 12 is sloped to define a substantially constant angle α of from about negative 15 degrees to about 15 degrees to counteract the tendency of the foot to either excessively supinate or to excessively pronate. As will be appreciated, the angle α is generally positive, as shown in FIG. 7, preferably from about 2 degrees to about 7 degrees for treating excessive pronation. Likewise, the angle α is negative, preferably from about −2 degrees to about −7 degrees for treating excessive supination.

A cutout 30 extends between the upper surface 16 and the lower surface 18. The cutout 30 is preferably substantially centrally located adjacent the heel end 22 for receiving a portion of the heel of the user. As will be noted, the cutout 30 preferably has a substantially tear-drop shape. The major length axis of the cutout 30 is positioned at an angle β relative to the center-line CL of the member 12. The angle β is preferably from about 25 to about 45 degrees, most preferably about 35 degrees.

For the purpose of example only, the wedge member 12 may have the following dimensions:

| Reference numeral | Dimension (in.) |
| --- | --- |
| a | 1 7/8 |
| b | 1 1/4 |
| c (width) | 2 1/2 |
| d (length) | 4 1/2 |
| e1 (greatest thickness of end 20) | 1/8 |
| e2 (smallest thickness of end 20) | 1/16 |
| f1 (greatest thickness of end 22) | 1/4 |
| f2 (smallest thickness of end 22) | 1/8 |

However, it will understood that the wedge member 12 may be provided in various other dimensions suitable for the purpose.

Figure 5:
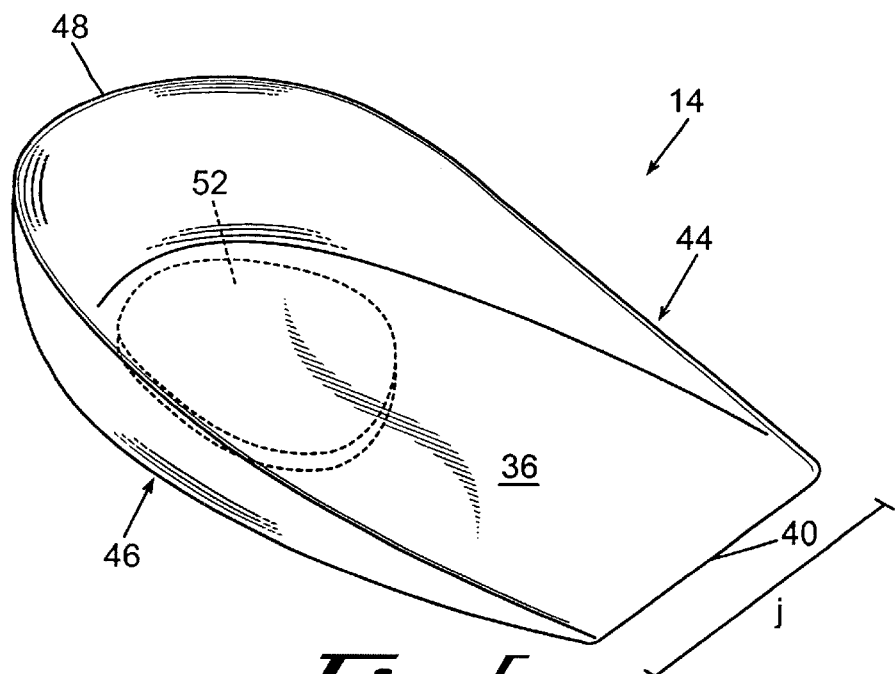
FIG. 5 is a top perspective view of a cup component of the device of FIG. 1.
Figure 6:
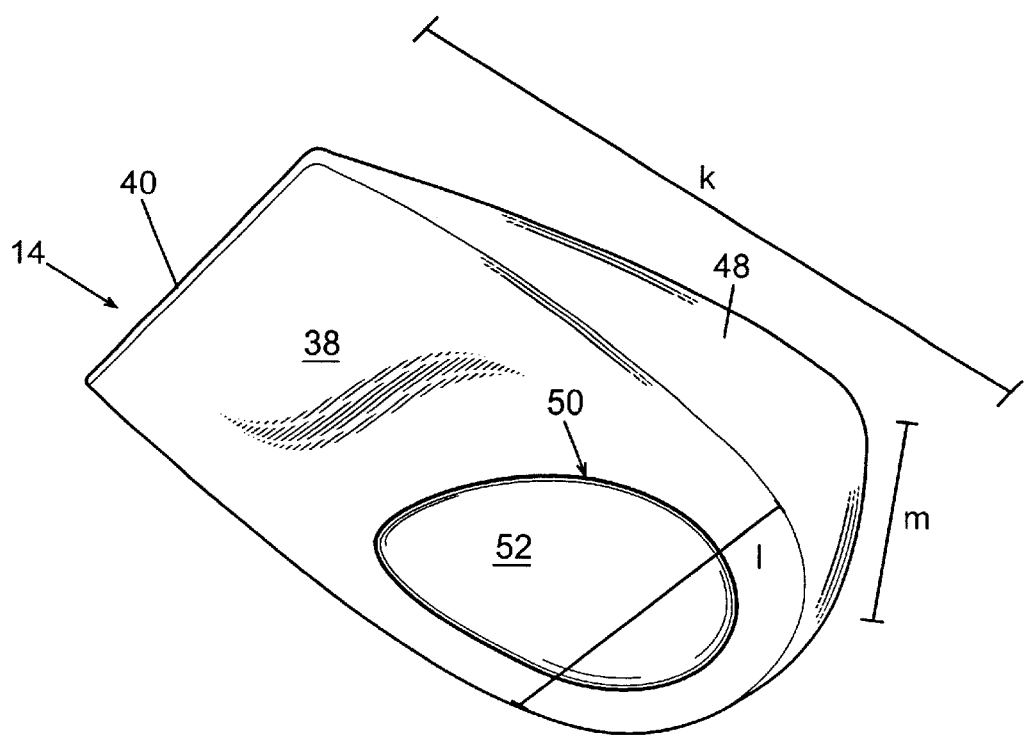
FIG. 6 is a bottom perspective view of the cup component of FIG. 5.

Turning to FIGS. 5 and 6, the cup member 14 is configured to be received onto the upper surface 16 of the wedge member 12 and includes a substantially planar upper surface 36, an opposite substantially planar lower surface 38, a generally straight front end 40, a generally curved heel end 42 and a pair of slightly curved sides 44 and 46.

A raised sidewall 48 preferably extends around the perimeter of the cup member 14 adjacent the end 42 and the sides 44 and 46 for surrounding the heel of the foot of the user. The sidewall 48 is preferably tapered in height, with the height adjacent the end 42 being greater than the height of the sidewall 48 adjacent the sides 44 and 46, with their heights decreasing in the direction toward the front end 40 such that the height of the sidewall adjacent front end 40 becomes about zero.

The cup member 14 is preferably of molded construction, made of a soft silicone material. The lower surface 38 includes a shallow blind bore 50 adjacent the lower surface 38 and extending toward the upper surface 36. The bore 50 preferably corresponds in size and shape to the cutout 30. The bore 50 is located so that it substantially overlies cutout 30 in the same orientation when the cup member 14 is positioned onto the wedge member 12. The bore 50 is preferably substantially filled with a cushion material 52, preferably a silicone material, that is even softer and more pliable than the surrounding silicone material. The material 52 is preferably introduced into the bore 50 during the molding step so that the resulting cup member 14 is a one-piece unit.

The cup member 14 preferably slopes uniformly in thickness along its length, with the thickness adjacent the front end 40 being from about 1/16 to about 1/8 inch, and the thickness adjacent the heel end 42 being from about 1/4 to about 1/2 inch. The thickness of the cushioning material is preferably substantially uniform.

For the purpose of example only, the cup member 14 may have the following dimensions:

| Reference numeral | Dimension (in.) |
| --- | --- |
| j (width of front end 40) | 2 1/4 |
| k (length) | 4 1/4 |
| l (width of heel end 42) | 2 1/2 |
| m (external height of sidewall 48 at end 42) | 1 1/2 |

However, it will understood that the cup member 14 may be provided in various other dimensions suitable for the purpose.

Returning now to FIG. 7, which is a representational posterior view showing an ankle joint 60 of a foot of a user (in skeletal representation) during use of the orthotic device 10. The ankle joint 60 is composed of three bones: the tibia 62 which forms the inside or medial portion of the ankle; the fibula 64 which forms the lateral or outside portion of the ankle; and the talus 66 underneath. The ankle joint 60 provides up and down motion of the foot. Beneath the ankle joint 60 is a second part of the ankle, referred to as the subtalar joint, which consists of the talus 66 on top and calcaneus or heel bone 68 on the bottom. The subtalar joint allows side to side motion of the foot, e.g, pronation and supination.

The ankle joint 60 shown in FIG. 7 is prone to excessive outward motion or pronation in the direction of the arrow 70. That is, the upper portion of the calcaneus 68 is prone to roll excessively outwardly in the direction of the arrow 70. As will be appreciated, the slope of the wedge member 12, as represented by the angle α is positive to counteract the tendency of the ankle to excessively pronate. Thus, during use, the wedge member 12 tends to reduce the outward rotation of the calcaneus 68.

Also during use, the calcaneus or heel bone 68 rests on the portion of the cup member 14 adjacent the cushion material 52. As the shoe contacts the ground during the gait cycle, i.e., during the heel-strike phase of the gait, the portion of the cup member overlying the cutout 30 of the wedge member, which includes the cushion material 52, is urged downwardly into the cutout 30. This is advantageous to provide a cushion to the heel as well as to disperse heel strike forces during the gait cycle. It has been observed that this can be comforting to a person suffering from heel pain, such as may result from the condition known as plantar fascitiis.

The foregoing description of certain exemplary embodiments of the present invention has been provided for purposes of illustration only, and it is understood that numerous modifications or alterations may be made in and to the illustrated embodiments without departing from the spirit and scope of the invention as defined in the following claims.

What is claimed is:

1. An orthotic device for inserting within a heel portion of a shoe of a user for inhibiting excessive pronation or excessive supination of a user's foot, and for comforting associated pain by cushioning a heel of the foot, the orthotic device comprising:

a wedge member having an upper surface, an opposite lower surface, a front end, a heel end, a pair of opposite sides, and a cutout extending between the upper surface and the lower surface, the upper surface of the wedge member being sloped between the opposite sides to define a substantially constant angle of from about negative 15 degrees to about 15 degrees to counteract the tendency of the foot to either excessively supinate or to excessively pronate; and a cup member positionable over the wedge member, the cup member comprising a first soft silicone material having an upper substantially continuous surface, an opposite lower substantially continuous surface, a front end, a heel end, a pair of opposite sides, and a shallow blind bore adjacent the lower surface of the cup member and extending toward the upper surface of the cup member and located so as to substantially overlie the cutout of the wedge member when the cup member is positioned adjacent the wedge member, the bore being substantially filled with a second soft silicone material.

2. The device of claim 1, wherein the wedge member is of one-piece construction and made of a relatively stiff, yet flexible polymeric material.

3. The device of claim 1, wherein the upper surface of the wedge member has a rugose topography to increase the coefficient of friction of the upper surface.

4. The device of claim 1, further comprising a raised rib extending around the perimeter of the wedge member adjacent the front end and the opposite sides.

5. The device of claim 1, wherein the cutout has a substantially teardrop shape.

6. The device of claim 1, wherein the cutout has a major length axis located at an angle of from about 25 to about 45 degrees relative to a center-line length axis of the wedge member.

7. The device of claim 1, wherein the cup member includes a raised sidewall substantially extending around the perimeter of the cup member, adjacent the heel end and the opposite sides of the cup member for surrounding the heel of the user during use of the device.

8. The device of claim 1, wherein the cup member is made of a silicone material.

9. The device of claim 1, wherein the shallow blind bore substantially corresponds in size and shape to the cutout.

10. The device of claim 1, wherein the shallow blind bore has a teardrop shape.

11. An orthotic device for inserting within a heel portion of a shoe of a user for inhibiting excessive pronation or excessive supination of a user's foot, and for comforting associated pain by cushioning a heel of the foot, the orthotic device comprising:

a wedge member having an upper surface, an opposite lower surface, a front end, a heel end, a pair of opposite sides, and a cutout extending between the upper surface and the lower surface, the upper surface of the wedge member being sloped between the opposite sides to define a substantially constant angle of from about negative 15 degrees to about 15 degrees to counteract the tendency of the foot to either excessively supinate or to excessively pronate; and a cup member positionable over the wedge member, the cup member comprising a body portion made of a first soft silicone material, the body portion having an upper substantially continuous surface, an opposite lower substantially continuous surface, a front end, a heel end, a pair of opposite sides, and a second soft silicone material positioned within the body portion and located so as to substantially overlie the cutout of the wedge member when the cup member is positioned adjacent the wedge member, wherein during use of the orthotic device the heel portion of the user's foot is positioned adjacent the second soft silicone material and the cutout so that during ambulation of the user the second soft silicone material is urged downwardly into the cutout.

12. The orthotic device of claim 11, wherein the cup members is one-piece construction with the first and second silicone material being co-molded.

* * * * *